United States Patent
St.Germain et al.

(10) Patent No.: US 9,610,372 B2
(45) Date of Patent: Apr. 4, 2017

(54) FLASH SAFE SEAL FEATURE

(71) Applicant: KONINKLIJKE PHILIPS N.V., Eindhoven (NL)

(72) Inventors: Mark David St.Germain, Dunstable, MA (US); Robert Alfred Feuersanger, Westford, MA (US); Juris Alex Grauds, Hull, MA (US); Paul Naumann, Providence, RI (US); Lisette Manrique Miller, Taunton, MA (US); Gerhard Andrew Foelsche, Rehoboth, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/415,655

(22) PCT Filed: Jul. 9, 2013

(86) PCT No.: PCT/IB2013/055622
§ 371 (c)(1),
(2) Date: Jan. 19, 2015

(87) PCT Pub. No.: WO2014/013386
PCT Pub. Date: Jan. 23, 2014

(65) Prior Publication Data
US 2015/0165077 A1 Jun. 18, 2015

Related U.S. Application Data

(60) Provisional application No. 61/673,418, filed on Jul. 19, 2012, provisional application No. 61/740,692, filed on Dec. 21, 2012.

(51) Int. Cl.
*A61L 2/10* (2006.01)
*A61L 2/00* (2006.01)
*A61N 5/00* (2006.01)
*A61N 5/06* (2006.01)

(52) U.S. Cl.
CPC ............... *A61L 2/10* (2013.01); *A61L 2/0047* (2013.01); *A61L 2202/121* (2013.01); *A61L 2202/14* (2013.01)

(58) Field of Classification Search
CPC .......................................................... A61L 2/10
USPC ............................................................ 422/24
See application file for complete search history.

(56) References Cited

U.S. PATENT DOCUMENTS

| | | |
|---|---|---|
| 6,730,113 B2 | 5/2004 | Eckhardt |
| 2002/0146343 A1 | 10/2002 | Jenkins |
| 2004/0034398 A1 | 2/2004 | Eckhardt et al. |
| 2006/0216193 A1 | 9/2006 | Johnson |

(Continued)

FOREIGN PATENT DOCUMENTS

WO 02102421 A1 12/2002

*Primary Examiner* — Kevin Joyner
*Assistant Examiner* — Holly Mull (57) ABSTRACT

A disinfection device includes a radiation lamp (112) having an aperture for delivering radiation. A flexible shroud (132) surrounds a perimeter of the aperture. The shroud includes a surface configured to deform and create a seal around the aperture when in contact with a target surface. A sensing circuit (120, 156) is configured to sense a state of the seal and enable the radiation lamp when the seal is complete.

17 Claims, 6 Drawing Sheets (56) References Cited

U.S. PATENT DOCUMENTS

2011/0098789 A1* 4/2011 Weckwerth .......... A61B 18/203
607/88
2011/0308034 A1 12/2011 Powers
2012/0283603 A1* 11/2012 Shapiro ................ A61N 7/00
601/2

* cited by examiner

FLASH SAFE SEAL FEATURE

CROSS-REFERENCE TO PRIOR APPLICATIONS

This application is the U.S. National Phase application under 35 U.S.C. §371 of International Application No. PCT/IB2013/055622, filed on Jul. 9, 2013, which claims the benefit of U.S. Provisional Patent Application No. 61/673,418, filed on Jul. 19, 2012 and U.S. Provisional Patent Application No. 61/740,692, filed on Dec. 21, 2012. These applications are hereby incorporated by reference herein.

BACKGROUND

Technical Field

This disclosure relates to medical instruments and more particularly to a flash disinfection system with a safe seal to reduce radiation exposure in a surrounding environment.

Description of the Related Art

Guidelines for the prevention of intravascular catheter-related infections report that a significant number of catheter related bloodstream infections occur each year, and that the cost of these infections is substantial, both in terms of morbidity and financial resources expended. The risk is greatest when medical devices penetrate the skin surface creating an ideal track for bacteria to migrate to sub-dermal tissue and the vasculature. This can lead to risk of serious infection.

The use of pulsed ultraviolet (UV) light energy may be employed to control skin level bacteria; however, UV exposure on skin comes with safety and efficacy issues. Uncontrolled exposure to UV light can be hazardous to human skin as well as represent an optical hazard from stray light.

SUMMARY

A disinfection device includes a radiation lamp having an aperture for delivering radiation. A flexible shroud surrounds a perimeter of the aperture. The shroud includes a surface configured to deform and create a seal around the aperture when in contact with a target surface. A sensing circuit is configured to sense a state of the seal and enable the radiation lamp when the seal is complete.

Another disinfection device includes a housing having an aperture. A radiation lamp is disposed within the housing and is configured to deliver radiation through the aperture. A flexible shroud is disposed on a distal end portion of the housing and surrounds a perimeter of the aperture. The shroud includes a surface configured to deform and create a seal around the aperture when in contact with a target surface. A sensing circuit is configured to sense a state of the seal and enable the radiation lamp when the seal is complete. A user interface is formed in the housing and configured to provide feedback to a user to establish a complete seal.

A method for disinfecting a target surface includes providing a radiation lamp in a housing having an aperture for delivering radiation, a flexible shroud surrounding a perimeter of the aperture, the shroud including a surface configured to deform to form a seal with a target surface and a sensing circuit configured to sense a state of a seal for the shroud; contacting the shroud against the target surface to be treated; applying pressure to deform the shroud; and if the shroud forms a complete seal with an amount of pressure on the target surface, activating the radiation lamp.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems and method are described that provide for radiation delivery to a skin site for disinfecting the site without leaking or delivering radiation to a surrounding area or environment. In one illustrative embodiment, an ultra-violet (UV) lamp includes a safety barrier that is provided between the UV lamp and an intended irradiation site, e.g., an intravenous catheter skin site. The barrier prevents triggering irradiation of the lamp if the barrier is not in full contact with the skin site. In this way, unintended human skin and/or eye exposure outside of the site is eliminated.

In one embodiment, a conformable shroud provides the safety barrier and a seal with a skin site and communicates the seal status electronically to a controller to prevent actuation of a 'flash' event for disinfection without an adequate seal. This assists a user or machine in positioning the instrument to complete the seal before radiation is emitted.

International safety standards seek to limit the unintentional exposure of human skin and eyes to harmful levels of electromagnetic radiation from light emitting devices. The present embodiments provide a feature that utilizes germicidal properties of the emitted radiation to control bacterial growth on human skin and provide a suitably opaque, sealed barrier between the target skin site and the rest of the patient, user, and others in close proximity to the device. In addition, the present principles prevent deliberate or unintended actuation of the device in the absence of a suitably safe seal to the skin site. A seal sensor senses the presence of sealed protection over a wide range of body types and medical instrument scenarios to appropriately conform to a target surface without obstruction.

It should be understood that the present invention will be described in terms of medical applications; however, the teachings of the present invention are much broader and are applicable to any system where disinfecting is needed. In some embodiments, the present principles are employed in medical applications; however, the present principles may have application in the food industry, pharmaceutical industry or any other application where disinfecting is needed. In particular, the present principles are applicable to disinfecting tissue surfaces such as skin or other biological surfaces.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1:
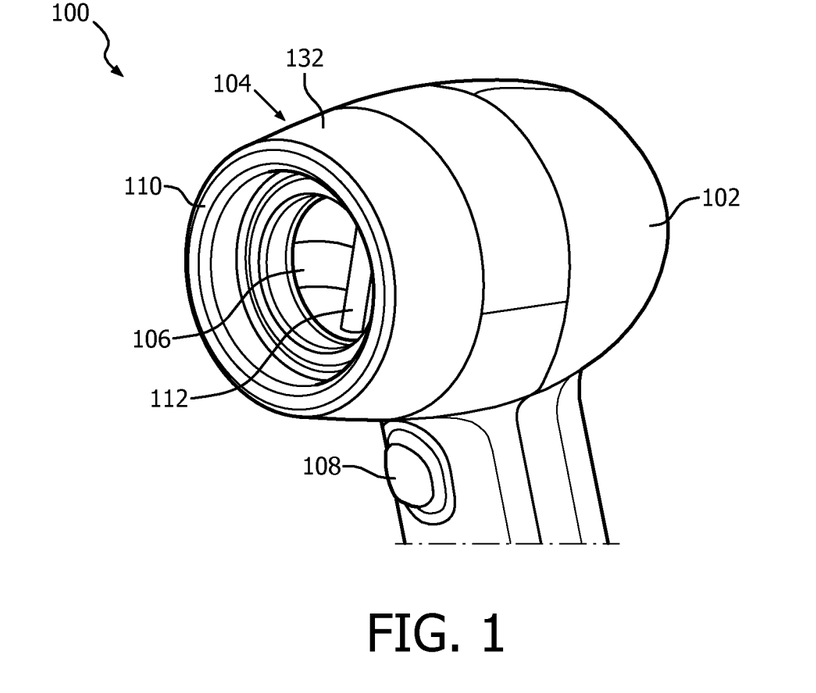
FIG. 1 is a perspective view of a disinfecting device in accordance with one embodiment.

Referring now to the drawings in which like numerals represent the same or similar elements and initially to FIG. 1, an illustrative disinfection lamp device 100 is shown in accordance with an exemplary embodiment. The lamp device 100 includes a housing 102 which contains an electromagnetic lamp or bulbs 112 for generating radiation. The radiation may include UV radiation for the purpose of destroying bacteria on a surface, such as a skin site during a medical procedure. The light is directed through an aperture 106, which may include a lens or other optics for directing light.

The housing includes an end portion 104, which circumferentially surrounds the aperture 106 and extends distally from the aperture 106. A distal end of the end portion 104 includes a shroud 132 having a contact surface 110. The contact surface 110 and shroud 132 are configured to seal against a surface to be treated. On an inside surface of the contact surface 110 (not shown), a conductive material 122 (FIG. 2) is provided. The conductive material 122 is adhered to or formed on an interior surface of the shroud 132. In one embodiment, the shroud 132 of the end portion 104 includes an elastomeric material of specific dimensions and material, which surrounds the light emitting aperture 106 and conforms to a target surface (e.g., skin surface) during use to, e.g., disinfect the target surface. In one embodiment, the elastomeric material of the shroud 132 may include rubber, such as silicone, or other flexible polymeric materials. The shroud 132 may be designed to provide a desired rigidity and dimensions to create a proper seal for a given application or applications. In one embodiment, the end portion may be removable and replaced with different types of shrouds 132.

The device 100 may include a manual trigger 108 to enable a user to activate the lamp or bulb 112 during use. In another embodiment, the trigger function is provided through a computer system or other hardware device. In accordance with one feature, the trigger 108 is disabled if insufficient pressure is applied against the contact surface 110, and/or if the shroud 132 is not sufficiently deflected.

The present embodiments may be employed with a specific medical device or application. The device 100 may be employed to maintain reduced bacterial levels, e.g., at a catheter skin site following CHG (Chlorhexidine gluconate) skin antisepsis or the like. The present embodiments may have applications with devices used in dermatological procedures or anywhere light energy levels intended for clinical efficacy exceed stated regulatory limits for unintended human exposure.

Figure 2:
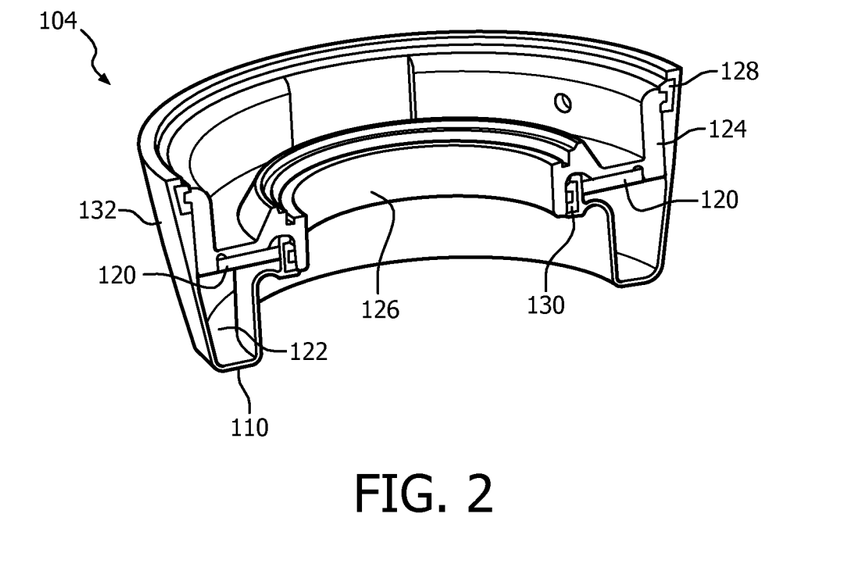
FIG. 2 is a cross-sectional perspective view of a shroud of the disinfecting device of FIG. 1 in accordance with the present principles.

Referring to FIG. 2, a perspective cross-sectional view of the end portion 104 is illustratively shown. When pressed against a target skin site, the end portion 104 or shroud 132 deflects or deforms, causing conductive material 122, e.g., in the form of a ring on an inside surface of the shroud 132, to make contact with and short circuit a plurality of individual pairs of contacts on a printed circuit board 120. The conductive material 122 may be printed or coated on the shroud 132 as needed. A printed circuit board 120 is mounted to a light emitting aperture support 124, which holds the board 120 in place. The pairs of contacts may include spaced apart conductive films, pads, beads or leads formed on the board 120 that are separated in an uncompressed state of the shroud 132 and connected in a compressed state by the conductive material 122 as it connects the pair(s) of contacts. The compressed state refers to a deflection of the shroud 132 when pressure is exerted against a target site in contact with the shroud 132. The pressure needs to be sufficient to deform the shroud 132 enough to make the connections. In one embodiment, all contact connections need to be made to ensure a complete seal around the shroud 132 before the source 112 can be activated. In this way, the shroud 132 can be designed to ensure that a good seal is formed between the target surface and the shroud 132 at the time the connections are made. The electrically conductive contact surface 122 may be formed by mask and spray application of a specific silicone and/or carbon based ink. Other conductive inks or deposited conductive materials may be employed.

The aperture support 124 includes a lens receiving portion 126 configured to receive a lens (not shown) or other optical components. The aperture support 124 may be coupled to the shroud 132 using snap rings 128 and 130 or other structures to connect the aperture support 124 to the shroud 132.

In one embodiment, the elastomeric shroud 132 includes a main shroud body molded of silicone over the retaining snap rings 128, 130. The snap rings 128 and 130 may include silicone of a higher durometer than the shroud 132. The material type, durometer, and the shape of each component, and in particular the shroud 132, are designed to accomplish a seal with an anticipated surface variation without obstructing delivered light energy dose. In addition, the materials are selected to be resistant to deterioration due to exposure to light energy.

Figure 3:
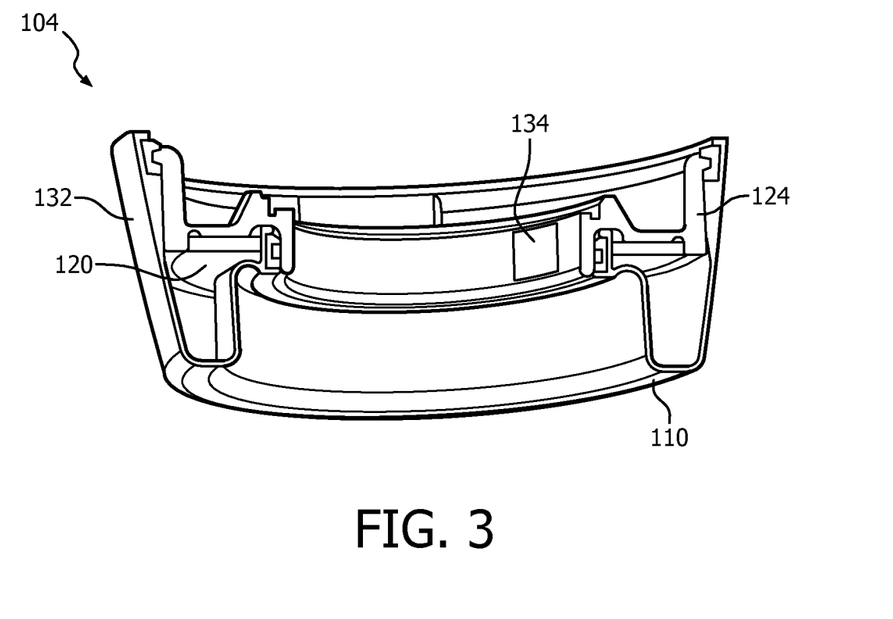
FIG. 3 is another cross-sectional perspective view of the shroud of the disinfecting device of FIG. 1 in accordance with the present principles.

Referring to FIG. 3, another perspective cross-sectional view of the end portion 104 is illustratively shown. FIG. 3 shows an under surface of the board where contacts, pads etc. may be formed. A lens or other optical element 134 is also shown mounted in aperture support 124.

Figure 4:
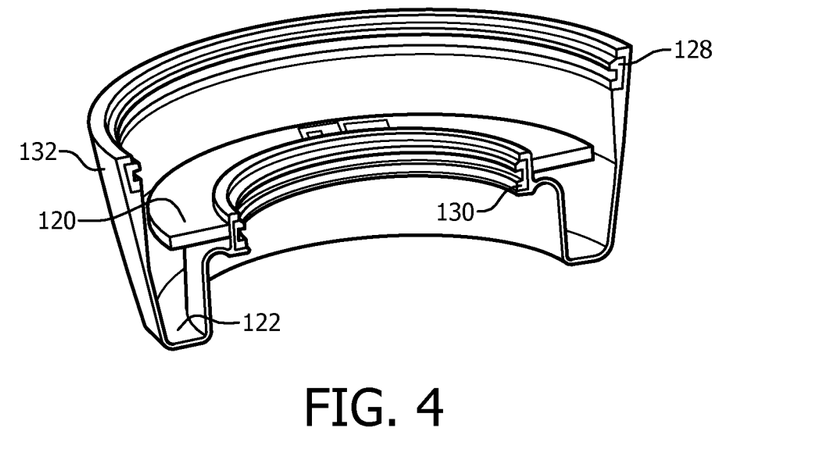
FIG. 4 is a cross-sectional perspective view of the shroud of the disinfecting device of FIG. 1 with an aperture mount removed in accordance with the present principles.

Referring to FIG. 4, another perspective cross-sectional view of the end portion 104 is illustratively shown with the aperture support 124 removed to show snap rings 128 and 130. The snap rings 128 and 130 are preferably snapped into annular slots formed within the shroud 132, and secure respective ends of the shroud 132. The printed circuit board 120 is also shown.

Figure 5:
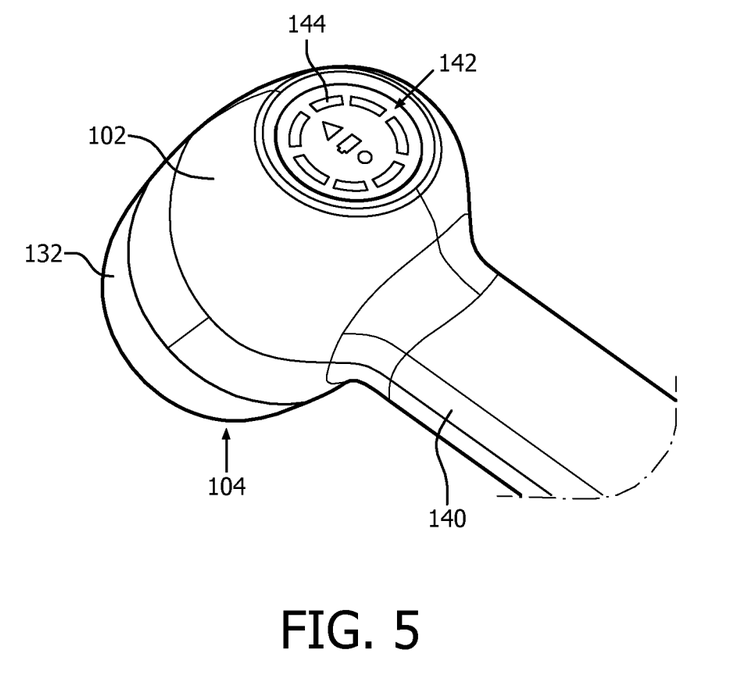
FIG. 5 is a perspective view of the disinfecting device of FIG. 1 showing a display or user interface formed in a housing in accordance with the present principles.

Referring to FIG. 5, the housing 102 and a handle 140 connected to the housing 102 include an internal volume where electronics, electronics running software, wiring, mechanical elements, etc. are included. In one embodiment, an additional printed circuit board (not shown) may be provided in the handle 140 of the device 100, which may be employed to detect the short circuit at each of the plurality of contact points, and, in turn, display the status of the contacts by lighting a representative light or light emitting diode (LED) segment 144 in a user display 142 mounted on the housing 102. The display 142 provides visual feedback to direct the user in applying force to the shroud 132 in a correct orientation and pressure to accomplish an appropriate seal. The device 100 is controlled to prevent actuation of the light energy dose unless all contact pairs are sensed 'closed'.

Figure 6:
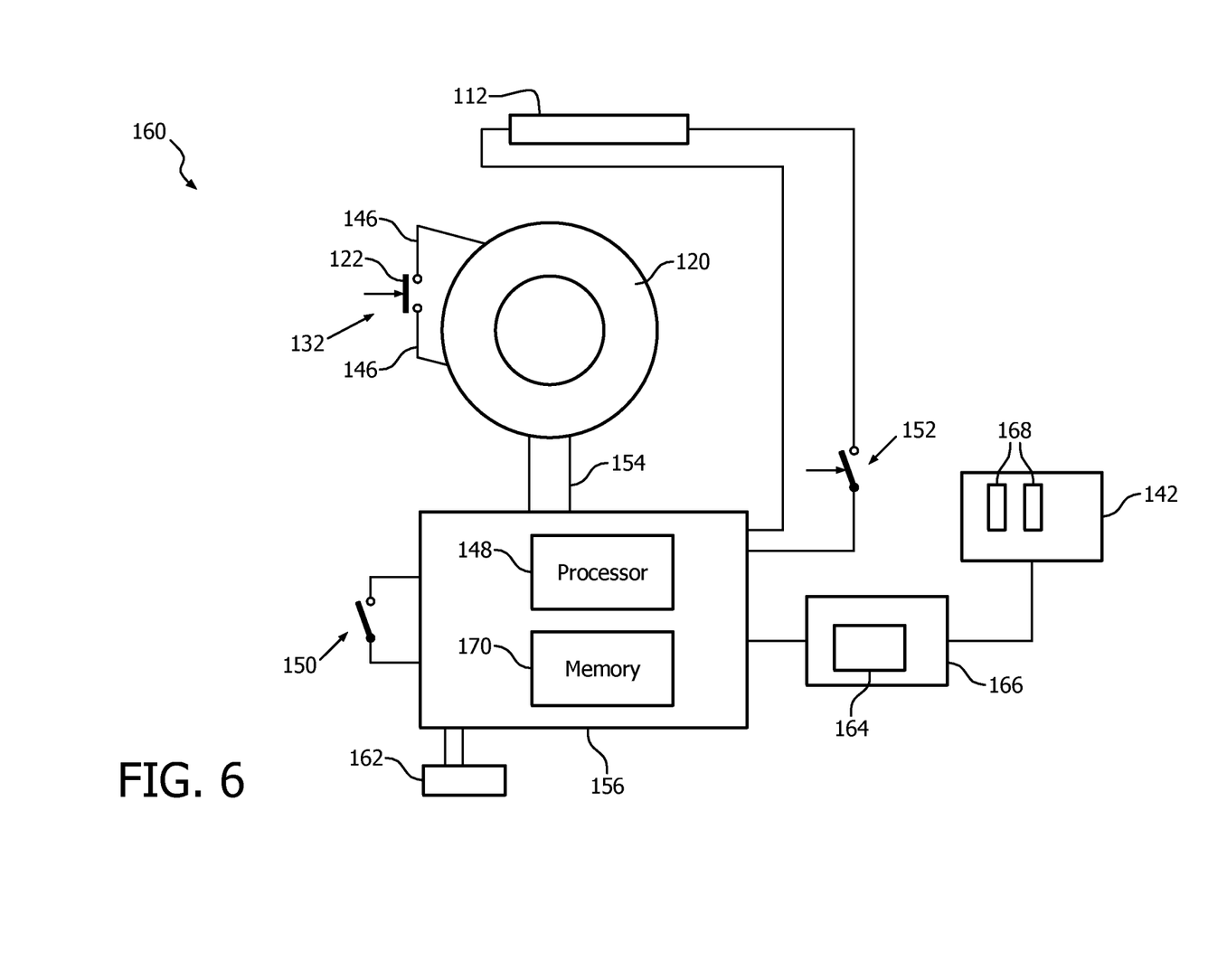
FIG. 6 is a schematic diagram showing illustrative circuitry for the disinfecting device of FIG. 1 in accordance with the present principles.

Referring to FIG. 6, a schematic diagram shows illustrative circuitry 160 for implementing an embodiment in accordance with the present principles. Circuitry 160 includes the printed wiring board 120, which may have an annular shape. The board 120 includes one or more contact pairs 146 on or connected to the printed circuit board 120. Only one pair of contacts 146 is shown for simplicity. The contacts 146 are shorted out by a portion of the conductive surface 122 when pressed into the contacts 146. The board 120 is connected by, e.g., a cable harness 154, to a second printed circuit board 156. The second printed circuit board 156 may include a controller 148, which senses the conduction status of each contact pair (146). The controller 148, in turn, drives an LED drive control chip 164 on a display printed circuit board 166, which drives LEDs 168, visible at the user interface or display 142. The drive control chip 164 may be integrated with the circuit board 156.

The circuitry 160 is powered by a power source 162. The power source 162 may be through other equipment or may include a direct connection to a power outlet or the like. During operation, the power source 162 is connected to board 156. Processor or controller 148 monitors its inputs to determine when the following events occur: 1) A trigger switch 150 is closed, and 2) all needed contact pairs 146 are shorted. If these conditions exist, the processor 148 closes a lamp control switch 152 to activate the bulb or lamp 112 to provide light to disinfect a surface. The processor 148 also lights LEDs 168 or alerts other indicators to provide feedback to the user as to which contact pairs 146 are shorted. The type and manner of communicating the status of the seal to a user interface (e.g., display 142) may take many forms. For example, the design of that display interface may include a liquid crystal display, a micromechanical element display, etc.

In addition, the display 142 and the circuitry 160, as a whole, may include additional elements not described in detail here. For example, the circuitry 160 and, in particular, the board 156 may include a memory device 170. The memory device 170 may include an operating system for running programs. Such programs may include software applications for adjusting the bulb output (e.g., pulse rate, intensity, etc.) or modes of operation for the device 100 as a whole (e.g., manual mode, automatic mode (when connected with other devices)). In another example, a temperature sensor or light sensor may be employed to monitor the temperature (or dose) of the device 100 and warn of overuse (using a software application and display 142).

The elements depicted in the FIGS., and in particular FIG. 6, may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Figure 7:
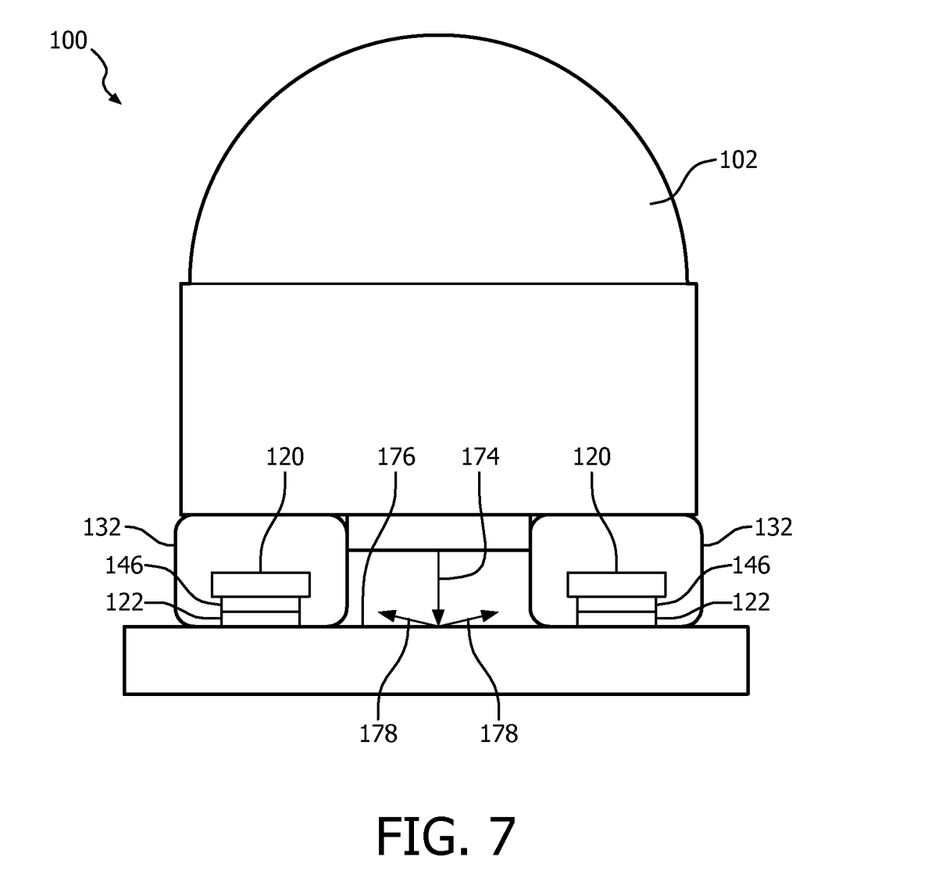
FIG. 7 is a partial cross-sectional view showing the shroud of the disinfecting device of FIG. 1 being compressed to reduce radiation loss in accordance with the present principles.

Referring to FIG. 7, a schematic diagram shows a cross-section of the shroud 132 compressed such that electrical contact is made between pads or contacts 146 on the board 120 and conductive material 122 formed on an interior surface of the shroud 132. As described above, once contact is made (short circuit) on all appropriate contact pairs, the device 100 is enabled for generating radiation 174 (e.g., UV light) for disinfecting a surface 176. By ensuring contact is made, a seal is formed between the shroud 132 and the surface 176. This seal acts as a barrier to reflected radiation 178 from the surface 176. In this way, users, the patient, technicians, physicians or any others present in the environment are protected from flash radiation (e.g., radiation 174 and 178).

It should be understood that alternative embodiments may be achieved with shapes and materials other than those illustratively described. Other conductive materials, either applied or molded into the conformable shroud 132 may be included to form the conductive material 122. In addition, the conductive material 122 may form a capacitive element and seal detection may be accomplished using a ring of capacitive touch sensors mounted inside of the distal end surface of the conformable shroud 132. In FIG. 6, a capacitive element may have the conductive material 122 acting as a first capacitor plate while the contacts 146 may be connected to form a second capacitive plate. The board 120 may monitor the capacitance to determine whether enough deformation has occurred in the shroud 132 to provide a proper seal. It should be noted that other electrical or electronic components may be employed instead of or in addition to those described herein. For example, strain gauges or pressure sensors may be wired into the shroud 132 to measure deflection or deformation.

Figure 8:
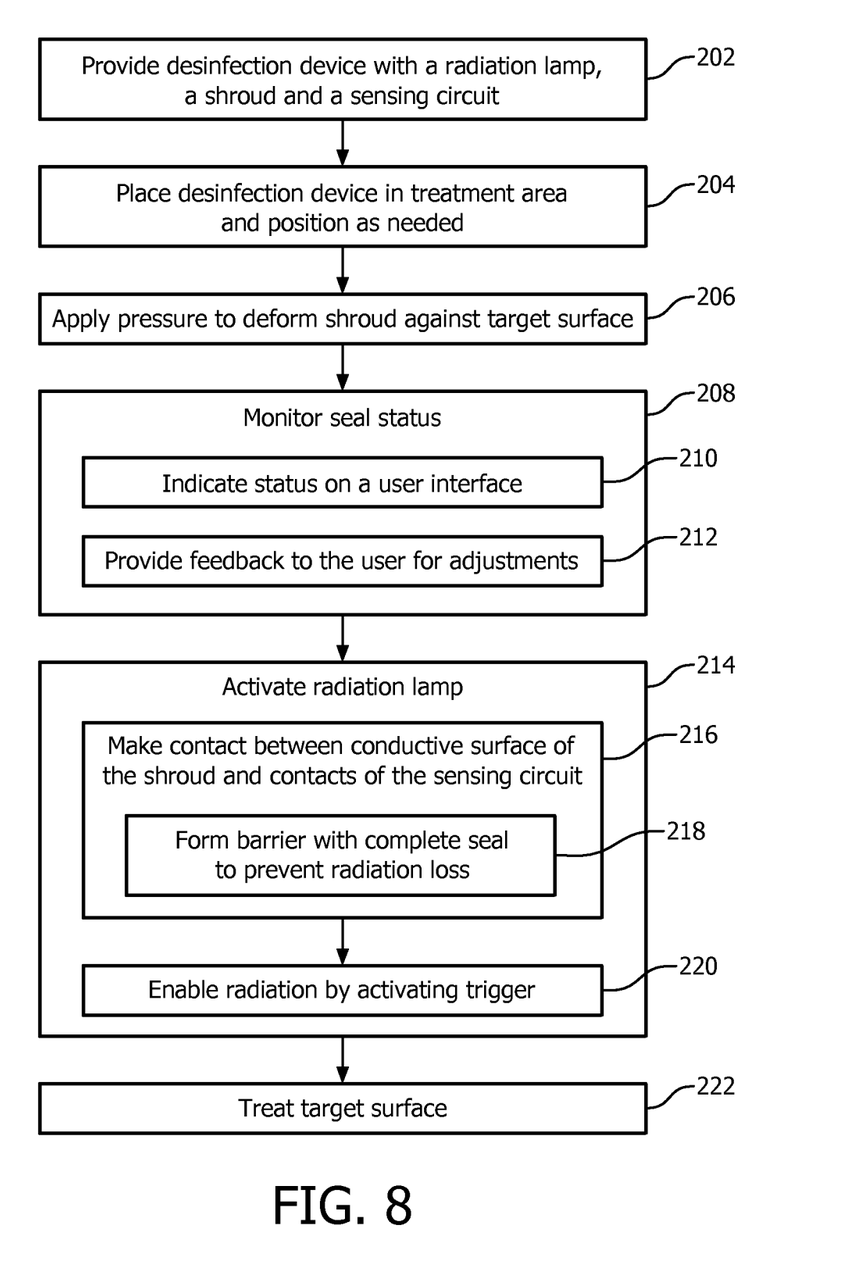
FIG. 8 is a block/flow diagram showing a method for employing a disinfecting device in accordance with illustrative embodiments.

Referring to FIG. 8, a method for disinfecting a target surface is illustratively shown in accordance with exemplary embodiments. It should be noted that, in some alternative implementations, the functions noted in the blocks of FIG. 8 may occur out of the order noted. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In block 202, a disinfection device in accordance with the present principles is provided. The device may include a radiation lamp in a housing having an aperture for delivering radiation. A flexible shroud surrounds a perimeter of the aperture, and the shroud includes a surface configured to deform. A sensing circuit is configured to sense a state of the seal. The radiation lamp may include an ultraviolet lamp.

In block 204, the shroud is positioned over a target surface, e.g., a skin site, table or other surface to be disinfected. Contact is made with the shroud against the target surface to be treated. In block 206, pressure is applied to deform the shroud.

In block 208, a seal status is monitored for a plurality of portions around the seal. In block 210, the seal status may be indicated for the plurality of portions on a user interface. In block 212, feedback may be provided to a user on the state of the seal to permit adjustments by the user to achieve the complete seal.

In block 214, the radiation lamp is activated only when the shroud forms a complete seal with a sufficient amount of pressure against the target surface. In block 216, the shroud includes an elastomeric material having a conductive surface on an interior portion. The pressure is applied to deform the shroud to change the seal status when contact is made between the conductive surface and contacts of the sensing circuit. In another embodiment, an amount of deformation may be measured in the shroud using capacitive elements, strain gauges, etc. In such a case, actual contact need not be made to change the status. Instead, a threshold amount may be employed such that when the threshold is achieved the seal status is changed. In block 218, the shroud includes an annular shape. A barrier is formed by the shroud to prevent radiation from escaping (radiation loss) when the shroud is in contact with the target surface and forms the complete seal.

In block 220, a trigger or switch may be provided and configured to enable the radiation lamp. The radiation lamp is activated when the trigger or switch is turned on, and the sensor circuit determines that the seal is complete. In block 222, the target surface is treated.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for a flash safe seal feature (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A disinfection device, comprising:
a radiation lamp;
a housing having an aperture for delivering radiation;
a flexible shroud surrounding a perimeter of the aperture, the shroud including a surface configured to deform and create a seal around the aperture when in contact with a target surface; and
a sensing circuit configured to sense a state of the seal and enable the radiation lamp when the seal is complete;
wherein the shroud includes an elastomeric material and a conductive surface on an interior portion and the sensing circuit includes contacts such that when the elastomeric material is deformed electrical contact is made between the conductive surface and the contacts which causes the sensing circuit to sense that the seal is complete; and
the conductive surface and the contacts are configured as a capacitive element such that when the elastomeric material is deformed electrical contact is made between the conductive surface and the contacts which causes the sensing circuit to sense that the seal is complete.

2. The device as recited in claim 1, wherein the sensing circuit includes:
   a trigger or switch configured to enable the radiation lamp when activated by a user and in accordance with the sensor circuit when the seal is complete.

3. The device as recited in claim 1, wherein the sensor circuit monitors a seal status of a plurality of portions around the seal, and the device further comprises an interface configured to indicate the seal status of the plurality of portions.

4. The device as recited in claim 3, wherein the interface includes:
   a display integrated with the housing for displaying the state of the seal.

5. The device as recited in claim 3, wherein the interface is formed in the housing.

6. The device as recited in claim 1, wherein the radiation lamp includes an ultraviolet lamp.

7. The device as recited in claim 1, wherein shroud includes an annular shape to provide a barrier for preventing radiation from escaping when in contact with the target surface.

8. The device as recited in claim 1, wherein:
   the radiation lamp is disposed within the housing and configured to deliver radiation through the aperture.

9. The device as recited in claim 8, further comprising a handle formed in the housing and including a trigger or switch configured to enable the radiation lamp when activated by a user and in accordance with the sensor circuit when the seal is complete.

10. The device as recited in claim 8, wherein the sensor circuit monitors a seal status of a plurality of portions around the seal, and wherein the user interface indicates the seal status of the plurality of portions.

11. The device as recited in claim 8, wherein the user interface includes a display integrated with the housing for displaying the state of the seal.

12. The device as recited in claim 8, wherein the radiation lamp includes an ultraviolet lamp.

13. The device as recited in claim 8, wherein shroud includes an annular shape to provide a barrier for preventing radiation from escaping when in contact with the target surface.

14. The device as recited in claim 8, further including:
   a user interface formed in the housing and configured to provide feedback to a user to indicate whether a complete seal has been established between the shroud and the target surface.

15. The device as recited in claim 1, wherein the shroud is disposed on a distal end of the housing.

16. The device as recited in claim 1, further including:
   a manually operable switch configured to supply power to the radiation lamp when manually operated; and
   wherein the sensing circuit is configured to block the manually operable switch from supplying power to the radiation lamp unless the sensing circuit senses that the seal is complete.

17. A disinfection device, comprising:
   a radiation lamp;
   a housing having an aperture for delivering radiation;
   a flexible shroud surrounding a perimeter of the aperture, the shroud including a surface configured to deform and create a seal around the aperture when in contact with a target surface; and
   a sensing circuit configure to sense a state of the seal and enable the radiation lamp when the seal is complete;
   wherein the shroud includes an elastomeric material and a conductive surface on an interior portion and the sensing circuit includes contacts such that when the elastomeric material is deformed electrical contact is made between the conductive surface and the contacts which causes the sensing circuit to sense that the seal is complete, and
   wherein the housing encloses the radiation lamp and has an end portion on which the shroud is disposed; and
   the conductive surface comprises a ring disposed on the interior portion of the shroud.

\* \* \* \* \*